United States Patent [19]

Adler

[11] 4,418,039
[45] Nov. 29, 1983

[54] SOLUTE TRANSFER TECHNIQUE

[75] Inventor: Harvey J. Adler, New City, N.Y.

[73] Assignee: Technicon Instruments Corporation, Tarrytown, N.Y.

[21] Appl. No.: 907,370

[22] Filed: May 19, 1978

Related U.S. Application Data

[63] Continuation-in-part of Ser. No. 754,773, Dec. 17, 1976, abandoned.

[51] Int. Cl.³ .............................................. G01N 31/08
[52] U.S. Cl. ..................................................... 422/82
[58] Field of Search ............. 203/1, 89; 159/DIG. 27, 159/49; 55/16; 210/22, 33, 31 C, 21; 422/50, 70, 82, 276, 290, 284

[56] References Cited

U.S. PATENT DOCUMENTS 3,743,103 7/1973 Isreeli et al. ........................... 422/82
3,957,651 5/1976 Kesting ............................. 210/31 C
3,966,410 6/1976 Jahnsen ............................. 210/31 C

FOREIGN PATENT DOCUMENTS 596912 4/1960 Canada ........................ 159/DIG. 27

OTHER PUBLICATIONS

Vaporization Through Porous Membranes, Findley, 59th National AICHE Meeting, 5/66.

Primary Examiner—Hiram Bernstein
Attorney, Agent, or Firm—S. P. Tedesco

[57] ABSTRACT

Transferring a solute from a first to a second liquid solvent, utilizing a membrane selectively permeable by a gas and impermeable by the liquids, which method includes the steps of: flowing the first liquid along said membrane, evaporating the first liquid across the membrane to dryness, said evaporation leaving a residue of the former solute on the membrane, and flowing the second liquid along the membrane for dissolving the residue.

7 Claims, 4 Drawing Figures

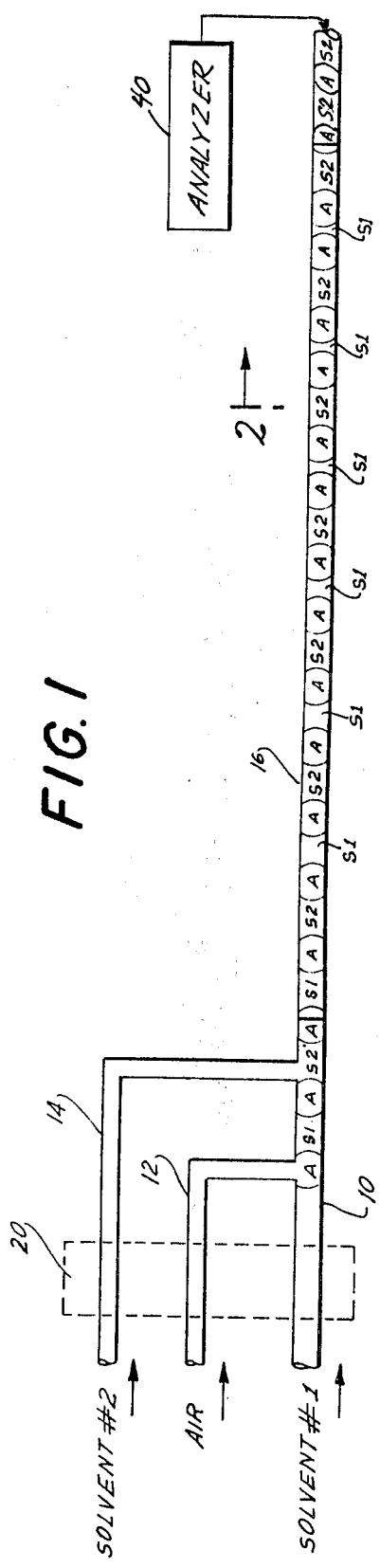
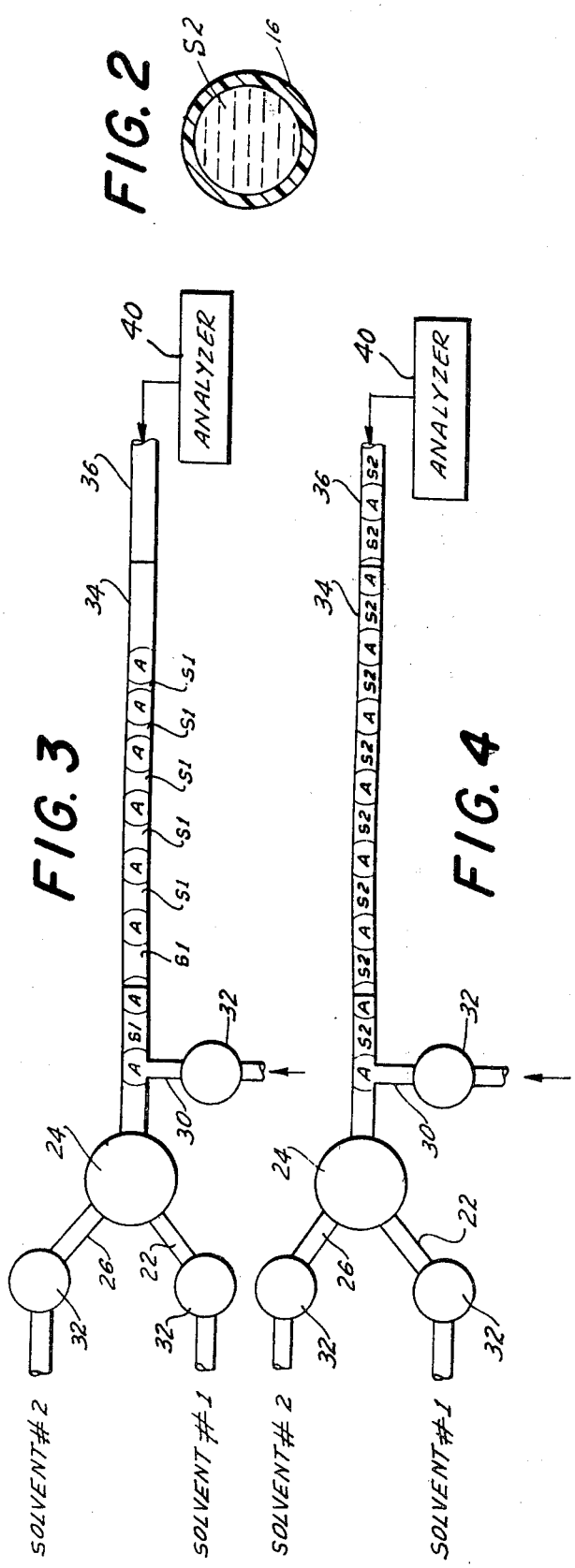

SOLUTE TRANSFER TECHNIQUE

RELATED APPLICATION

This application is a continuation-in-part of the previously filed application, Ser. No. 754,773, filed Dec. 17, 1976, now abandoned.

This invention relates to the transfer of a solute from a first to a second liquid solvent, utilizing a membrane selectively impermeable to such liquids. It includes the steps of flowing the first liquid along the membrane, evaporating the first liquid across the membrane to leave a residue from the solute and flowing the second liquid along the membrane for dissolving therein the residue. Heretofore, it has been common to transfer a substance across a membrane from a donor stream to a recipient stream as in dialysis. The transferred substance tends to reach equilibrium across the membrane in such a dialysis process.

It is known to employ in dialysis a bundle of dialysis tubes which bundle is interposed in a sleeve such that the dialysate passing through a wall of the hollow tubing is conveyed away in the sleeve in which a receipient stream flows. It is also known, in solvent extraction techniques, that a sample in a solvent may be extracted into a smaller volume of a second solvent in which some concentration of the sample may occur. However, neither of these techniques involves evaporation of the first solvent. The present invention may include, as previously indicated, the evaporation step to leave the former solute as a residue on the membrane, and flowing the second liquid along the membrane for dissolving therein the residue.

It is an object of the invention to provide an improved method and apparatus for such solvent transfer. Further objects of the invention will be apparent from the following detailed description of the invention.

In the drawing:

FIG. 1 is a somewhat schematic fragmentary view illustrating apparatus embodying the invention;

FIG. 2 is an enlarged view taken on line 2—2 of FIG. 1;

FIG. 3 is a view similar to FIG. 1 illustrating modified form and showing a fluid stream flowing through apparatus; and FIG. 4 is a fragmentary view illustrating a different fluid stream flowing through the apparatus.

As shown in FIG. 1, compressible pump tubes 10, 12 and 14 extend through a peristalic pump 20. The pump tube 10 has an inlet connected to a nonillustrated source of a first solvent liquid. The inlet end of pump tube 12 is open to the ambient air for the supply of air to the tube 12. The inlet end of tube 14 is connected to a nonillustrated source of a second solvent liquid. The first solvent has a solute therein which it is desired to transfer therefrom to the second solvent. The tubes 12 and 14 are coupled to the tube 10 downstream from the pump 20 in the illustrated manner. Thus, the continuous operation of the pump 20 effects flowing segments of the first solvent which segments are designated S1 and flowing segments of air, designated A, bracketing each segment S1 in the tube 10. A pair of air segments A also bracket each segment of the second solvent, which last-mentioned segments are designated S2, flowing in tube 10. The output of tube 10 flows along a membrane which is shown structured as a tube 16 having an inlet coupled to the outlet of tube 10. The tube 16 may be formed of silicone, for example, and is selectively permeable to the first solvent and impermeable to air and the second solvent. The outlet of the tube 16 is coupled to the inlet of tube 18 which may be structured of glass, and it is to be understood that the tubes 10 and 18 are not permeable by gas or liquids.

The aforementioned supply of the first solvent liquid may be from a conventional sampler. The sample or solute may be a fat-soluble vitamin, such as vitamin A or vitamin D, the first solvent may be hexane, and the second solvent may be methanol or water. The ultimate analysis of the sample or solute may be for example, by an ultraviolet spectrophotometer or by colorimeter as shown generally by analyzer block 40 connected to respective conduits 18 and 36 of FIGS. 1, 3 and 4. As indicated in FIG. 1, the first solvent segments S1 containing the solute flow along the tube 16 in such manner that, at the interface of these segments with the wall of tube 16, segments S1 pass or diffuse through the wall of tube 16 and vaporize in the ambient atmosphere. In this manner, the segments S1 become progressively smaller as they flow along the tube 16 to the extent that such segments ultimately disappear, leaving a nonillustrated residue of the former solute on the wall of tube 16. The segments S2 of the second solvent dissolve such residue and flow from the tube 16 to the tube 18, as previously described. Other examples of the first solvent are pentane, chloroform, heptane, tetrahydrofuran, benzene and ethyl acetate. Such solvents when vaporized, pass through the wall of tube 16. It will be evident from the foregoing that the solute in the first solvent must be soluble in the second solvent in such a solute transfer technique.

FIGS. 3 and 4 illustrate a modified form of the invention wherein glass tubes 22, 26 have their respective inlet ends coupled to sources of first and second solvents, respectively, and have their outlet ends connected to a three-way valve 24. A solute is present in the first solvent. The valve 24 has an output coupled to glass tube 28. A tube 30 has an inlet end exposed to ambient air and an outlet end connected to the tube 28. Selectively operated pumps 32 are interposed in the tubes 22, 28 and 30, respectively. The tube 28 has an outlet coupled to the inlet of a silicone tube or the like, indicated at 34, of the type similar to the previously-described tube 16. The outlet end of the tube 34 is coupled to an inlet of a glass tube 36. The aforementioned construction of the apparatus of FIGS. 3 and 4 is such that the valve 24 may be opened for passage therethrough of either the first solvent, containing the solute, or the second solvent. In FIG. 3, there is shown the passage through the last-mentioned apparatus of the first solvent wherein air delivered from the tube 30 into the tube 28 segments the first solvent, with the pumps 32 interposed in the tubes 22, 30 in operation. The first solvent is progressively evaporated, passing through the tube 34 in a manner previously described with reference to the apparatus in FIG. 1. However, if desired, the evaporation may be short of dryness. The evaporation may be such as to only concentrate the solute in the first solvent for later preparatory use or analysis on exit from the tube 36. In the form of FIG. 3, the first solvent may be completely evaporated to leave the solute as a nonillustrated residue on the internal wall structure of tube 34, with the air segments combining and flowing off through the tube 36. Subsequent to complete evaporation of the first solvent segments S1, the valve 24 is operated to place tube 26 in communication with the tube 34 for the flow of the second solvent segments S2 through the tube 34 as shown in FIG. 4. The pumps 32 interposed in the tubes 26, 30 are operated, with the pump 32 interposed in the tube 22 shut down. The second solvent segments S2 dissolve the residue of the former solute on the internal wall structure of the tube 34 to convey the solute through the tube 36. The apparatus of FIG. 3 is particularly well suited to receive through the tube 22 an effluent stream from a chromotography column but in no way is limited to such use.

If desired, the first solvent may be mixed with a third solvent which may not evaporate through the membrane or tube 34. In such case, an evaporation of the first solvent, the solute is concentrated in the third solvent.

While several forms of the invention have been illustrated and described, it will be apparent, especially to those versed in the art, that the invention may take other forms and is susceptible to various changes in details without departing from the principles of the invention.

What is claimed is:

1. Apparatus for transferring a solute from a first solvent to a second solvent, comprising: a selectively permeable tubular membrane, said membrane being impermeable to said solute and to said second solvent, first means flowing said first solvent along said membrane for evaporation to dryness of said first solvent across said membrane to leave a residue of all of said solute on an inner surface wall of said membrane, second means for flowing said second solvent along said tubular membrane to dissolve said residue, and analyzing means for analyzing said second solvent containing said solute containing said solute residue, said second means including means for segmenting said first solvent with segments of an immiscible gas, said membrane being impermeable to said immiscible gas, and means for introducing said second solvent as discrete segments intermediate successive segments of said first solvent and separated therefrom by immiscible gas segments.

2. A apparatus as defined in claim 1, wherein said membrane is formed of silicone.

3. A apparatus as defined in claim 1, wherein said first solvent is selected from a group consisting of: pentane, hexane, chloroform, heptane, tetrahydrofuran, benzene and ethyl acetate.

4. A apparatus as defined in claim 1, wherein said second solvent is methanol.

5. A apparatus as defined in claim 1, wherein said second solvent is water.

6. The apparatus of claim 1, wherein said analyzing means is a spectrophotometer.

7. The apparatus of claim 1, wherein said analyzing means is a colorimeter.

* * * * *